United States Patent
Bowman et al.

[11] 3,973,030
[45] Aug. 3, 1976

[54] ANTIASTHMATIC 5,6-BENZOISOINDOLINE COMPOSITIONS

[75] Inventors: Robert Mathews Bowman, Summit; Heinz Werner Gschwend, New Providence, both of N.J.

[73] Assignee: Ciba-Geigy Corporation, Ardsley, N.Y.

[22] Filed: Oct. 29, 1973

[21] Appl. No.: 410,940

[52] U.S. Cl. .............................. 424/274; 260/326.1
[51] Int. Cl.² ...................................... A61K 31/40
[58] Field of Search ................. 424/274; 260/326.1

[56] References Cited
UNITED STATES PATENTS
3,166,570  1/1965  Winthrop ........................... 260/319

FOREIGN PATENTS OR APPLICATIONS
2,259,498  12/1971  Germany ........................ 260/326.1

OTHER PUBLICATIONS
Quinkert et al. Chem. Abst., vol. 65, 8853–8856 (1966).

Primary Examiner—Stanley J. Friedman
Attorney, Agent, or Firm—Joseph G. Kolodny; Theodore O. Groeger; John J. Maitner

[57] ABSTRACT

4-Phenyl-9,9a-dihydro-5,6-benzoisoindolines, e.g. those of the formula

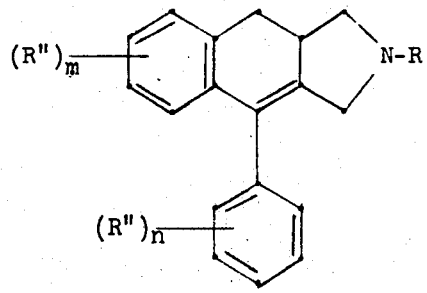

R = H, alkyl, alkenyl or (hydroxy or amino)-alkyl,
R'' = H, alkyl, OH, alkanoyloxy, alkoxy, ½ alkylenedioxy, benzyloxy, halogeno, $CF_3$, $NO_2$ or amino
$m, n$ = 1 to 4
or salts thereof are also antiallergic agents.

2 Claims, No Drawings

ANTIASTHMATIC 5,6-BENZOISOINDOLINE COMPOSITIONS

BACKGROUND OF THE INVENTION

2-Benzyl-4-phenyl-9,9a-dihydro-5,6-benzo-1 or 3-isoindolinones have been described by Klemm et al in J. Heterocyclic Chem., 9, 1215 (1972) as "N-benzylcyclolignan lactams", which are further examples of their "studies on the intramolecular Diels-Alder reaction". Surprisingly, it has been found that the 2-desbenzyl, or other N-substituted derivatives of said lactams, and reduced derivatives thereof, exhibit valuable pharmacological properties.

SUMMARY OF THE INVENTION

The present invention concerns and has for its object the provision of new 4-phenyl-9,9a-dihydro-5,6-benzoisoindolines, more particularly of those corresponding to Formula I

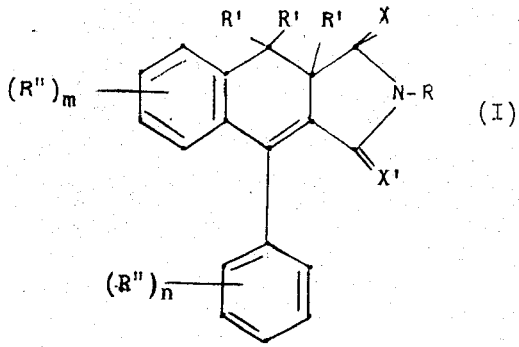

wherein R is hydrogen, lower alkyl, lower alkenyl or (hydroxy or amino)-lower alkyl, each of R' is hydrogen or lower alkyl, each of R'' is hydrogen, lower alkyl, hydroxy, lower alkanoyloxy, lower alkoxy, ½ lower alkylenedioxy, benzyloxy, halogeno, trifluoromethyl, nitro, amino or di-lower alkylamino, each of $m$ and $n$ is an integer from one to four and each of X and X' is two hydrogens, hydrogen and lower alkyl or oxo, or therapeutically acceptable acid addition salts thereof of corresponding pharmaceutical compositions and of methods for the preparation and application of these products, which are useful antiallergic, antiasthmatic and antihistaminic agents.

DESCRIPTION OF THE PREFERRED EMBODIMENTS

A lower alkyl group R, R' or R'' is preferably methyl, but also ethyl, n- or i-propyl or-butyl: straight or branched pentyl, hexyl or heptyl. A lower alkenyl group R is preferably allyl, and also methallyl, 2- or 3-butenyl. A (hydroxy or amino)-lower alkyl group R is preferably q-(hydroxy, amino, mono- or di-lower alkylamino)-lower alkyl, wherein $q$ is an integer from 2 to 4, e.g. 2-, 3- or 4-(hydroxy, amino, mono- or dimethylamino)-ethyl, -propy or -butyl. A lower alkanoyloxy group R'' is preferably acetoxy, but also propionyloxy n or i-butyryloxy. A lower alkoxy or alkylenedioxy group R'' is preferably methoxy or methylenedioxy respectively, but also ethoxy, n or i-propoxy or butoxy: 1,1- or 1,2-ethylenedioxy or -propylenedioxy. A halogen atom R'' is preferably chloro, but also fluoro or bromo, and a di-lower alkylamino group R'' represents preferably dimethylamino. One or both of X and X' are preferably hydrogen, or one thereof is hydrogen or hydrogen and methyl, and the other, preferably X', is oxo. The term "lower", referred to above and hereinafter in connection with organic radicals or compounds respectively, defines such with up to 7, preferably up to 4 carbon atoms. Moreover, the symbols R, R', R'', X and X' may all be equal, e.g. hydrogen, or one, or more than one thereof, may represent any of the other radicals listed for them above.

Acid addition salts of the basic compounds of Formula I are derived from therapeutically acceptable inorganic or organic acids, preferably of those listed below.

The compounds of the invention exhibit valuable pharmacological properties. Apart from anti-inflammatory activity, they exhibit predominantly antiallergic, antiasthamtic and antihistaminic effects. This can be demonstrated either in vitro or in vivo tests, using advantageously mammals, such as mice, rats, guinea pigs or dogs as test objects, or isolated organs thereof. The in vitro tests are performed either with human leukocytes of volunteers who are allergic to ragweed pollen, or with the guinea pig ileum in a standard organ bath, e.g. physiological saline. In the former test, as described by Lichtenstein et al, J. Exp. Med. 120, 507 (1964), the aqueous leukocyte suspension, when treated with a purified ragweed pollen extract (antigen E), releases histamine, which can be estimated fluorometrically. The compounds of the invention, especially the 2-methyl-4-(3,4,5-trimethoxyphenyl)-9,9a-dihydro-5,6-benzoisoindoline hydrochloride, being illustrative thereof, when added to said leukocyte suspension, or ileum bath, in an amount to reach concentrations down to about $10^{-5}$ molar, inhibit the histamine release of the leukocytes, or the histamine-induced iluem-contraction respectively, thus indicating antiallergic and antihistaminic effects, which latter are also confirmed by the classical in vivo tests in mice, rats and guinea pigs. With enteral or parenteral, e.g. oral or intravenous, doses of said compounds, for example in the range between 0.1 and 200 mg/kg/day, preferably between about 1 and 100 mg/kg/day, especially with about 5 or 10 mg/kg/day i.v., or with about 50 or 100 mg/kg/day p.o. doses of said hydrochloride, significant protection against egg-albumin anaphylaxis, or passive cutaneous anaphylaxis is achieved.

Antiasthmatic activity is estimated in dogs, who are naturally sensitive to ascaris antigens, causing asthma-like syndroms after inhalation of said nebulized antigens. The compounds of the invention are administered orally or intraveneously in about the same dosage ranges mentioned above, about 30–60 minutes after antigen-challenge, and efficacy is observed by the change in the dogs' respiratory-rate and airway-resistance.

Accordingly, the compounds of the invention can be applied enterally or parenterally, e.g. by inhalation of a nebulized aqueous solution, or by peroral, subcutaneous, intramuscular or intraveneous administration, in about the dosage range shown above. According to the test results obtained, they are useful antiasthmatic, antiallergic and antihistaminic agents. They are also valuable intermediates of other preparations, preferably of pharmacologically useful products.

Preferred compounds of the invention are those of Formula I, in which R is hydrogen, lower alkyl, lower alkenyl or q-(hydroxy, amino, mono- or di-lower alkylamino)-lower alkyl, wherein $q$ is an integer from 2 to 4, each of R' is a similar or dissimilar member of hydrogen and methyl, each of R'' is a similar or dissimilar member of hydrogen, hydroxy, alkyl, alkanoyloxy or alkoxy with up to 4 carbon atoms, ½ methylenedioxy, benzyloxy, fluoro, chloro, bromo, trifluoromethyl, nitro, amino or dimethylamino, each of $m$ and $n$ is an integer from 1 to 3 and each of X and X' is two hydrogens or oxo, or therapeutically acceptable acid addition salts thereof.

More active are the compounds of Formula II

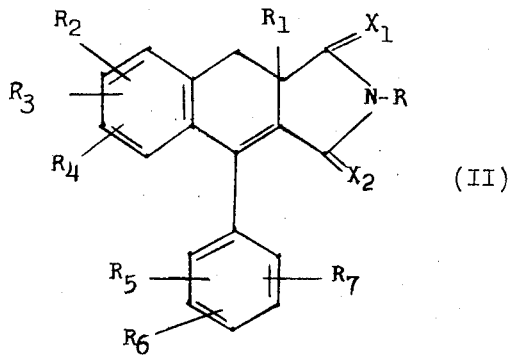

wherein R is alkyl or alkenyl with 1 to 4 carbon atoms, $R_1$ is hydrogen or methyl, each of $R_2$, $R_3$, $R_4$, $R_5$, $R_6$ and $R_7$ is a member selected from the group of hydrogen, methyl, hydroxy, acetoxy, methoxy or benzyloxy, or one of $R_2$, $R_3$ and $R_4$, or $R_5$, $R_6$ and $R_7$ is fluoro, chloro, trifluoromethyl, amino or dimethylamino and the others are hydrogen, or two of $R_2$, $R_3$ and $R_4$, or $R_5$, $R_6$ and $R_7$, when adjacent and taken together, represent methylenedioxy, and each of $X_1$ and $X_2$ is two hydrogens or one thereof is oxo, or therapeutically acceptable acid addition salts thereof.

Outstanding are those compounds of Formula II, wherein R is methyl or ethyl, $R_1$ is hydrogen or methyl, each of $R_2$, $R_3$, $R_4$ is hydrogen, methyl, hydroxy, acetoxy or methoxy, or one thereof is fluoro or chloro, and the other two are hydrogen, each of $R_5$, $R_6$ and $R_7$ is hydrogen or methoxy, or $R_3$ and $R_4$, as well as $R_5$ and $R_6$, when taken together, are methylenedioxy, and $R_2$ and $R_7$ are hydrogen, and both of $X_1$ and $X_2$ are two hydrogens, or therapeutically acceptable acid addition salts thereof.

The most active compounds of the invention are those of Formula II, wherein each of $R_1$, $R_2$, $X_1$ and $X_2$ is hydrogen, R is methyl, each of $R_3$ and $R_4$ is hydrogen or methoxy in 6- and 7-position and each of $R_5$, $R_6$ and $R_7$ is methoxy in the 3'-,4'-and 5'-positions, or therapeutically acceptable acid addition salts thereof.

The compounds of this invention are prepared according to known methods, preferably by:

a. heating the amide of Formula III

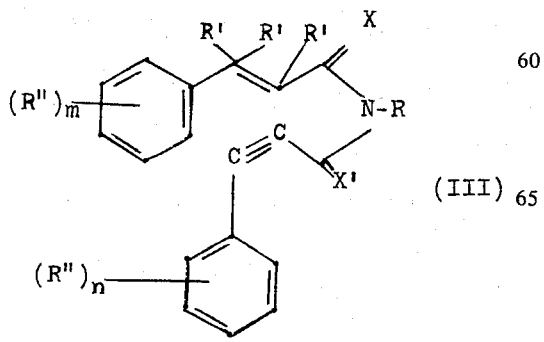

wherein at least one of X and X' is oxo and the other symbols have the meaning given above, or b. dehydrating the carbinol of Formula IV

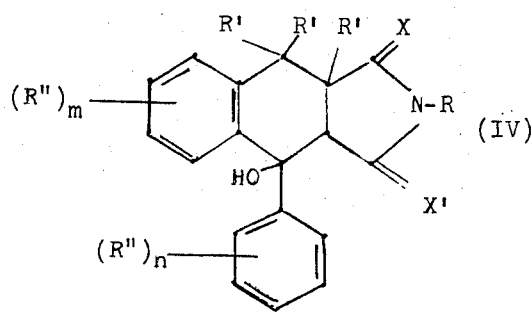

with an acidic dehydrating agent and, if desired, converting any resulting compound into another compound of the invention.

The heating of compounds III is preferably performed in solution or suspension of any inert diluent, for example a hydrocarbon, or a halogenated derivative thereof, an ester or anhydride, e.g. toluene, chloroform, ethyl acetate or acetic anhydride. Cyclization of III to I may even occur in the formation of III, for example in the condensation of corresponding cinnamylamines with phenylpropiolic acids or reactive functional derivatives thereof, e.g. halides, simple or mixed anhydrides, preferably those obtained from alkyl haloformates, e.g. ethyl chloroformate; or of cinnamyl halides with phenylpropiolic acid amides, e.g. as described by Klemm et al.

Dehydration of compounds IV is performed with the usual acidic dehydrating agents, for example, aqueous mineral acids, e.g. hydrochloric, sulfuric or polyphosphoric acid; organic sulfonic acids, e.g. benzene- or p-toluenesulfonic acid. Said compounds IV can be obtained photochemically by irradiation of corresponding 2-CHR'$_2$-benzophenones and N-R-$\alpha$-R'-maleimides with ultraviolet light, e.g. that emitted from medium pressure mercury lamps and, if desired, reducing in the resulting carbinol one or both oxo groups with complex light metal hydrides, e.g. lithium aluminum hydride, in suitable media, e.g. tetrahydrofuran and/or diethyl ether.

Any resulting compound of the invention so obtained can be converted into another compound of Formula I according to methods known per se. Thus, for example, any resulting compound in which X and/or X' is oxo, R is lower alkenyl, or R'' is benzyloxy or nitro, can be reduced; oxo groups preferably with complex light metal hydrides, e.g. as shown for the carbinols above, and the remaining groups preferably with catalytically activated hydrogen, e.g. hydrogen in the presence of palladium, in order to obtain alkyl, hydroxy or amino compounds respectively. Resulting phenolic hydroxy compounds can be esterified in the usual manner, e.g. by treating them with lower alkanoic acid halides or anhydrides, either in the presence or absence of bases, such as alkali metal hydroxides or tert. amines. Any resulting primary or secondary amine or amide, e.g. compounds with R = H, can be N-substituted with reactive esters of the corresponding alcohols R—OH, e.g. the halides or sulfonates thereof mentioned above, in order to obtain the corresponding N-substituted derivatives.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, at atmospheric or superatmospheric pressure. Condensing agents are especially used in the reaction with reactive esters or acid derivatives, in order to eliminate the acid formed. They are basic agents, for example, alkali or alkaline earth metal carbonates or lower alkoxides, or organic nitrogen bases, advantageously aliphatic or aromatic tert. amines, such as tri-lower alkylamines or pyridines, e.g. triethylamine, pyridine or collidine.

Basic compounds of the invention are obtained in the free form or in the form of their salts, depending on the conditions under which the process is carried out; the salts are also included in the present invention. Salts that are obtained can be converted into free bases in known manner, for example, with alkalies or ion exchangers. Free bases that are obtained can be converted into salts by reaction with inorganic or organic acids, especially those that are suitable for the formation of therapeutically useful salts. Such acids are, for example, mineral acids, e.g. hydrochloric, hydrobromic, sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic,4-aminosalicyclic, pamoic, nicotinic, methanesulfonic, ethanesulfonic, hydroxyethanesulfonic, ethylenesulfonic, halogenbenzenesulfonic, toluenesulfonic, naphthalenesulfonic, sulfanilic or cyclohexylsulfamic acid; methionine, tryptophan, lysine or arginine.

These or other salts of the invention, for example, the picrates, can also be used for purification of the bases obtained; the bases are converted into salts, the salts are separated and the bases are liberated from the salts. In view of the close relationship between the free compounds and the compounds in the form of their salts, whenever a free base is referred to in this context, a corresponding salt is also intended, provided such is possible or appropriate under the circumstances.

The invention further includes any variant of the present process, in which an intermediate product obtainable at any stage of the process is used as starting material and any remaining steps are carried out, or the process is discontinued at any stage thereof, or in which the starting materials are formed under the reaction conditions, or in which the reaction components are used in the form of their salts. For example, the amines, imides or hydroxy compounds (phenols) mentioned, can be used in the form of their alkali metal salts. Mainly, those starting materials should be used in the process of the invention that lead to the formation of those compounds indicated above as being specially valuable.

Starting materials or final products that are mixtures of isomers, can be separated into the single isomers by methods in themselves known, e.g. by fractional crystallization and/or chromatography. Racemic products can likewise be resolved into the optical antipodes, for example by separation of diastereomeric derivatives thereof, e.g. by the fractional crystallization of d- or -tartrates, -malates, -mandelated or -camphorsulfonates, e.g. salts or 2-acyl derivatives.

The pharmacologically active compounds of the invention are useful in the manufacture of pharmaceutical compositions comprising an effective amount thereof in conjunction or admixture with excipients suitable for either enteral, parenteral or topical application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, d) disintegrants, e.g. starches, agar, alginic acid or its sodium salt, enzymes of the binders or effervescent mixtures and/or e) adsorbents, colorants, flavors and sweeteners. Injectables and inhalants are preferably aqueous isotonic solutions or suspensions, and suppositories or ointments are liquid or solid fatty emulsions or suspensions. They may be sterilized and/or contain adjuvants, such as preserving stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50%, of the active ingredient.

The following examples are intended to illustrate the invention and are not to be construed as being limitations thereon. Temperatures are given in degrees Centigrade, and all parts wherever given are parts by weight.

EXAMPLE 1

The solution of 18.1 g of N-cinnamyl-N-methyl-3,4,5-trimethoxyphenylpropiolamide in 300 ml of toluene is refluxed for 6 hours and evaporated under reduced pressure. The residue is triturated with diethyl ether-petroleum ether (1:1) and recrystallized from ethyl acetate-n-hexane, to yield the 2-methyl-4-(3,4,5-trimethoxyphenyl)-9,9a-dihydro-5,6-benzo-3-isoindolinone of the formula

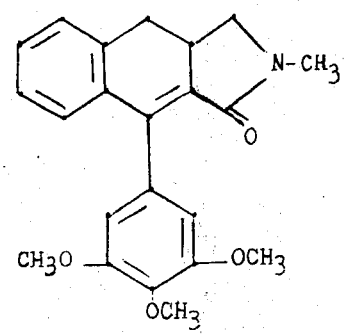

melting at 193°–195°.

The starting material can be prepared according to the following two methods:

A. The solution of 10.0 g of N-methyl-3,4,5-trimethoxyphenylpropiolamide in 80 ml of dimethylformamide is added dropwise to the suspension of 1.05 g of sodium hydride in 10 ml of dimethylformamide while stirring and cooling with ice. The mixture is stirred for 1 hour at room temperature whereupon the solution of 8.0 g of cinnamyl bromide in 40 ml of dimethylformamide is added dropwise and stirring is continued for 15 hours at room temperature. The mixture is poured into the solution of 20 ml of 3N hydrochloric acid in 600 ml of water and the whole is extracted with 250 ml of toluene. The extract is washed with 2N aqueous sodium hydroxide and saturated aqueous sodium chloride, dried and filtered, to yield the desired toluene-solution of the N-cinnamyl-N-methyl-3,4,5-trimethoxyphenyl-propiolamide.

Instead of the cinnamyl bromide, the chloride may also be used. Illustrative of its preparation is the following procedure: To the Grignard reagent, prepared from 2.25 g of magnesium, 9.75 g of vinyl bromide and 50 ml of tetrahydrofuran, the solution of 10.2 g of 4-methoxybenzaldehyde in 75 ml of diethyl ether is added dropwise while stirring under nitrogen and cooling with ice. The mixture is stirred for 2 hours at room temperature, again cooled, and 12 ml of saturated aqueous ammonium chloride are added dropwise. The resulting suspension is filtered, the filtrate dried and evaporated, to yield the 4-methoxy-α-vinylbenzyl alcohol.

The solution of 11.5 g thereof in 60 ml of diethyl ether is added dropwise to the mixture of 9.1 g of thionyl chloride, 12.2 g of pyridine and 150 ml of diethyl ether while stirring and cooling with ice. After stirring for 5 minutes at 0°–5°, the mixture is washed with ice-cold N-hydrochloric acid, N aqueous sodium carbonate and saturated aqueous sodium chloride. It is dried, evaporated, the residue taken up in warm petroleum ether, the solution cooled and the precipitate collected, to yield the 4-methoxycinnamyl chloride melting at 70°–72°. B) To the solution of 11.8 g of 3,4,5-trimethoxyphenylpropiolic acid in 50 ml of tetrahydrofuran, 7.1 g of triethylamine are added while stirring, followed by 50 ml of diethyl ether. The mixture is cooled with ice and to the resulting suspension the solution of 5.4 g of ethyl chloroformate in 25 ml of diethyl ether is added during 5 minutes. The mixture is stirred for 15 minutes at 0°–5°, whereupon the solution of 7.35 g of N-methylcinnamylamine in 35 ml of diethyl ether is added dropwise, followed by 80 ml of methylene chloride. The mixture is stirred for 30 minutes and allowed to warm to room temperature. It is washed with N hydrochloric acid, N aqueous sodium hydroxide and saturated aqueous sodium chloride, dried and evaporated under reduced pressure, to yield the N cinnamyl-N-methyl —3,4,5-trimethoxyphenylpropiolamide.

Other N-methyl-cinnamylamines can be prepared as follows: To the solution of 5.55 g of di-isopropylamine in 60 ml of diethyl ether, 35 ml of 1.6 molar n-butyl lithium in hexane are added dropwise while stirring at −20° under nitrogen. Thereupon the solution of 6.9 g of N-ethylidenecyclohexylamine in 50 ml of diethyl ether is added dropwise at −20°, followed by the solution of 10.6 g of 4-benzyloxy-benzaldehyde in 50 ml of diethyl ether and 10 ml of tetrahydrofuran at −70°. The mixture is stirred for 1 hour at room temperature, washed with 50 ml of water and stirred with 100 ml of water and 50 ml of acetic acid for 8 hours at room temperature. The ethereal layer is collected, washed with water, N hydrochloric acid, 2N aqueous sodium hydroxide and saturated aqueous sodium chloride, dried and evaporated, to yield the 4-benzyloxycinnamaldehyde.

To the mixture of 12.0 g thereof, 9 g of magnesium sulfate and 40 ml of benzene, 68 ml of 1.6 molar methylamine in benzene are added and the suspension is stirred at room temperature for 6 hours. It is filtered and the filtrate added dropwise to the solution of 1.9 g of sodium borohydride in 100 ml of anhydrous ethanol while stirring and cooling with ice. Stirring is continued for 15 hours at room temperature, the mixture cooled again, 10 ml of concentrated hydrochloric acid are added and the solution evaporated under reduced pressure. The residue is taken up in N aqueous sodium hydroxide, the mixture extracted with diethyl ether, the extract dried and evaporated, to yield the N-methyl-4-benzyloxycinnamylamine; the cyclohexysulfamate of which melts at 150°–151°.

EXAMPLE 2

According to the methods described in Example 1 the following compounds of Formula II are prepared from equivalent amounts of the corresponding starting materials, obtained according to method A or B; $X_1=H_2$, $X_2=O$, bz=benzyl

| No | R | $R_1$ | 8-$R_2$ | 7-$R_3$ | 6-$R_4$ | 3'-$R_5$ | 4'-$R_6$ | 5'-$R_7$ | Method | m.p. °C |
|---|---|---|---|---|---|---|---|---|---|---|
| 1 | $CH_3$ | H | H | H | H | H | H | H | A | 173–175 |
| 2 | " | H | H | H | F | H | H | H | A | 210–212 |
| 3 | " | H | H | H | Cl | H | H | H | A | 247–248 |
| 4 | " | H | Cl | H | H | H | H | H | B | 186–187 |
| 5 | " | H | H | H | H | H | H | Cl | A | 166–167 |
| 6 | " | H | H | H | $OCH_3$ | H | H | H | B | 183–185 |
| 7 | " | H | H | $OCH_3$ | " | H | H | H | A | 176–177 |
| 8 | " | H | H | " | " | $OCH_3$ | $OCH_3$ | $OCH_3$ | A | 158–160 |
| 9 | " | H | H | H | " | " | " | " | A | 193–194 |
| 10 | " | H | H | O—$CH_2$—O | " | " | " | " | A | 260–263 |
| 11 | " | H | H | " | " | H | H | H | A | 230–233 |
| 12 | " | H | H | H | H | H | O—$CH_2$—O | " | A | 195–197 |
| 13 | " | H | H | H | Obz | H | H | H | A | 198–200 |
| 14 | " | H | H | H | " | $OCH_3$ | $OCH_3$ | $OCH_3$ | B | 189–190 |
| 15 | " | $CH_3$ | H | H | H | " | " | " | B | 136–138 |
| 16 | " | H | H | H | $N(CH_3)_2$ | " | " | " | B | 181–182 |
| 17 | " | H | H | H | $NO_2$ | H | H | H | B | 243–244 |
| 18 | allyl | H | H | H | H | $OCH_3$ | $OCH_3$ | $OCH_3$ | B | 139–141 |

EXAMPLE 3

12.1 g of 2-methyl-4-(3,4,5-trimethoxyphenyl)-9,9a-dihydro-5,6-benzo-3-isoindolinone are added portionwise to the stirred suspension of 2.5 g of lithium aluminum hydride in 300 ml of diethyl ether while cooling with ice. Thereupon the mixture is refluxed for 15 hours, again cooled, and 2.5 ml of water, 2.5 ml of 15% aqueous sodium hydroxide and 7.5 ml water are added dropwise in this order. It is filtered, the filtrate dried, evaporated, and the residue taken up in the minimum amount of acetone. The solution is acidified with ethereal hydrogen chloride, diluted with diethyl ether and the resulting precipitate collected, to yield the 2-methyl-4-(3,4,5-trimethoxyphenyl)-9,9a-dihydro-5,6-benzoisindoline hydrochloride melting at 212°–215°.

EXAMPLE 4

Analogous to the method described in Example 3, the following compounds of Formula II are prepared from equivalent amounts of reactants: $X_1=X_2=H_2$, bz=benzyl

| No | R | $R_1$ | 8-$R_2$ | 7-$R_3$ | 6-$R_4$ | 3'-$R_5$ | 4'-$R_6$ | 5'-$R_7$ | Salt | m.p. °C |
|----|---|-------|---------|---------|---------|----------|----------|----------|------|---------|
| 1 | $CH_3$ | H | H | H | H | H | H | H | citrate | 174–175 |
| 2 | " | H | H | H | F | H | H | H | " | 132–134 |
| 3 | " | H | H | H | Cl | H | H | H | " | 184 (dec.) |
| 4 | " | H | Cl | H | H | H | H | H | maleate | 180–181 |
| 5 | " | H | H | H | H | H | H | Cl | citrate | 159–160 |
| 6 | " | H | H | H | $OCH_3$ | H | H | H | " | 176–177 |
| 7 | " | H | H | $OCH_3$ | $OCH_3$ | H | H | H | HCl | 202–204 |
| 8 | " | H | H | " | " | $OCH_3$ | $OCH_3$ | $OCH_3$ | — | 131–133 |
| 9 | " | H | H | H | " | " | " | " | — | 157–158 |
| 10 | " | H | H | O—$CH_2$—O | | H | H | H | citrate | 182–184 |
| 11 | " | H | H | H | H | H | O—$CH_2$—O | | HCl | 110 |
| 12 | " | H | H | H | Obz | H | H | H | citrate | 179–180 |
| 13 | " | H | H | H | $NH_2$ | H | H | H | 2 HCl | 250 (dec.) |
| 14 | " | H | H | H | $N(CH_3)_2$ | $OCH_3$ | $OCH_3$ | $OCH_3$ | — | NMR 278 |
| 15 | n—$C_3H_7$ | H | H | H | H | " | " | " | — | 124–126 |

EXAMPLE 5

The suspension of 6.4 g of 2-methyl-6-nitro-4-phenyl-9,9a-dihydro-5,6-benzo-3-isoindolinone, 0.5 g of 10% palladium on charcoal and 300 ml of ethanol is hydrogenated at room temperature and atmospheric pressure until the hydrogen uptake ceases. It is filtered and the filtrate evaporated, to yield the 6-amino-2-methyl-4-phenyl-9,9a-dihydro-5,6-benzo-3-isoindolinone, showing in the NMR-spectrum a singlet at 2.80 ppm.

EXAMPLE 6

The suspension of 11.2 g of 2-allyl-4-(3,4,5-trimethoxyphenyl)-9,9a-dihydro-5,6-benzo-3-isoindolinone, 1.1g of 10% palladium on charcoal and 300 ml of ethanol is hydrogenated at room temperature and atmospheric pressure until the hydrogen uptake ceases. It is filtered and the filtrate evaporated, to yield the 2-n-propyl-4-(3,4,5-trimethoxyphenyl)-9,9a-dihydro-5,6-benzo-3-isoindolinone, showing in the NMR-spectrum a singlet at 6.5 ppm; m.p. 124°–126°.

EXAMPLE 7

The mixture of 0.61 g of 4-hydroxy-2-methyl-4-phenyl-3a,4,9,9a-tetrahydro-5,6-benzoisoindolin-1,3-dione, 0.38 g of p-toluenesulfonic acid monohydrate and 10 ml of benzene is stirred and refluxed on a water-trap for 5 hours. After cooling it is washed with 2N aqueous sodium hydroxide and saturated aqueous sodium chloride, dried and evaporated, to yield the 2-methyl-4-phenyl-9,9a-dihydro-5,6-benzoisoindolin-1,3-dione melting at 212°–214°.

The starting material is prepared as follows: The mixture of 9.8 g of 2-methylbenzophenone, 6.6 g of N-methyl-maleimide and 500 ml of acetonitrile is deoxygenated by bubbling a slow stream of dry nitrogen through it for 40 minutes. Thereupon the solution is irradiated under nitrogen for 18 hours at 25°–30° with a 450 Watt medium pressure mercury lamp, fitted with a Pyrex-filter. The lamp is contained in the center immersion-well of the vessel, the water-cooled jacket of which also serves as a coolant for the reaction mixture. It is evaporated under reduced pressure, the residue taken up in 150 ml of chloroform, the mixture filtered through a 2 × 10 column of silica gel and the column eluted with chloroform. The eluate is evaporated and the residue recrystallized from ethanol, to yield the 4-hydroxy-2-methyl-4-phenyl-3a,4,9,9a-tetrahydro-5,6-benzoisoindolin-1,3-dione melting at 171°–173°.

EXAMPLE 8

0.25 g of 2-methyl-4-phenyl-9,9a-dihydro-5,6-benzoisoindolin-1,3-dione are added to the suspension of 0.2 g of lithium aluminum hydride in 30 ml of diethyl ether and the mixture is stirred at room temperature for 15 hours. Thereupon 1 ml of water is added dropwise, the mixture filtered, the filtrate dried and evaporated, to yield the 2-methyl-4-phenyl-9,9a-dihydro-5,6-benzoisoindoline melting at 106°–109°, it is identical with that obtained according to Example 4; the citrate thereof melts at 174°–175°.

EXAMPLE 9

The suspension of 0.85 g of 4-hydroxy-4-phenyl-3a,4,9,9a-tetrahydro-5,6-benzoisoindoline and 8 ml of 3N sulfuric acid is heated at the steam cone for 10 hours. After cooling it is made basic with 3N aqueous sodium hydroxide and the mixture extracted with diethyl ether. The extract is dried, combined with 3.5 ml of 2N etheral sulfuric acid and the precipitate collected, to yield the 4-phenyl-9,9a-dihydro-5,6-benzoisoindoline sulfate melting at 264°–266°.

The starting material is prepared as follows: The solution of 20.2 g of 4-hydroxy-4-phenyl-3a,4,9,9a-tetrahydro-5,6-benzoisoindolin-1,3-dione in 200 ml of tetrahydrofuran is added dropwise to the stirred suspension of 8.0 g of lithium aluminum hydride in 50 ml of tetrahydrofuran. After stirring at room temperature over night 8 ml of water, 8 ml of 15% aqueous sodium hydroxide and 24 ml of water are added in this order while stirring and cooling with ice. The suspension is filtered and the filtrate evaporated, to yield the 4-hydroxy-4-phenyl-3a,4,9,9a-tetrahydro-5,6-benzo-3-isoindolinone showing in the I.R.-spectrum a strong band at 1680 $cm^{-1}$.

The solution of 18.0 g thereof in 100 ml of tetrahydrofuran and 100 ml of diethyl ether is added dropwise to the stirred suspension of 6.5 g of lithium aluminum hydride in 50 ml of diethyl ether. The mixture is stirred for 15 hours at room temperature and worked up as shown above. The filtrate obtained is extracted with N hydrochloric acid, the extract made basic with aqueous sodium hydroxide and partitioned between diethyl ether. The organic solution is washed with saturated aqueous sodium chloride, dried and evaporated, to yield the 4-hydroxy-4-phenyl-3a,4,9,9a-tetrahydro-5,6-benzoisoindoline melting at 148°–150°.

EXAMPLE 10

The solution of 10.6 g of N-methyl-N-(3,4-dimethoxycinnamyl)-3,4,5-trimethoxyphenylpropiolamide in 200 ml of benzene is refluxed for 10 hours and evaporated under reduced pressure. The residue is taken up in 150 ml of hot diethyl ether and on standing the 2-methyl-4-(3,4,5-trimethoxyphenyl)-6,7-dimethoxy-9,9a-dihydro-5,6-benzo-3-isoindolinone crystallizes. It is filtered off, dried and melts at 158°–160°; in the NMR-spectrum it shows a band at 7.10 ppm.

The mother liquor contains a smaller amount of the coproduced 2-methyl-4-(3,4,5-trimethoxyphenyl)-5,6-dimethoxy-9,9a-dihydro-5,6-benzo-3-isoindolinone, showing the corresponding NMR-band at 6.83 ppm.

The starting material is prepared as follows: To the mixture of 19.2 g of 3,4-dimethoxycinnamaldehyde, 24 g of magnesium sulfate and 100 ml of benzene, 6.2 g of methylamine in 120 ml of benzene are added and the suspension is stirred at room temperature for 8 hours. It is filtered and the filtrate added dropwise to the solution of 3.8 g of sodium borohydride in 200 ml to anhydrous ethanol while stirring and cooling with ice. Stirring is continued over night at room temperature, the mixture cooled again, 25 ml of concentrated hydrochloric acid are added and the solution evaporated under reduced pressure. The residue is taken up in 150 ml of water the solution washed with diethyl ether, made basic with sodium hydroxide and the mixture extracted with diethyl ether. The extract is dried and evaporated, to yield the N-methyl-3,4-dimethoxycinnamylamine as an oil; the cyclamate thereof melts at 145°–147°.

To the solution of 11.6 g of 3,4,5-trimethoxyphenylpropiolic acid in 60 ml of tetrahydrofuran, 6.0 g of triethylamine are added while stirring, followed by 60 ml of diethyl ether. The mixture is cooled with ice and to the resulting suspension the solution of 5.35 g of ethyl chloroformate in 30 ml of diethyl ether is added dropwise. The mixture is stirred for 15 minutes at 0°–5°, whereupon the solution of 9.7 g of N-methyl-3,4-dimethoxycinnamylamine in 30 ml of diethyl ether is added dropwise, followed by 50 ml of methylene chloride. The mixture is stirred for 30 minutes at room temperature and washed with N hydrochloric acid, 2N aqueous sodium hydroxide and saturated aqueous sodium chloride, dried and evaporated under reduced pressure, to yield the N-methyl-N-(3,4-dimethoxycinnamyl)-3,4,5-trimethoxyphenylpropiolamide.

EXAMPLE 11

13.2 g of 2-methyl-4-(3,4,5-trimethoxyphenyl)-6,7-dimethoxy-9,9a-dihydro-5,6-benzo-3-isoindolinone are added portionwise to the stirred suspension of 1.42 g of lithium aluminum hydride in 200 ml of diethyl ether and 70 ml of benzene while cooling with ice. Thereupon the mixture is refluxed for 15 hours, again cooled, and 1.4 ml of water, 1.4 ml of 15% aqueous sodium hydroxide and 4.2 ml of water are added dropwise in this order. It is filtered, the filtrate dried, evaporated, and the residue taken up in 150 ml of acetone containing 0.5 ml of water. The solution is acidified with ethereal hydrogen chloride and the resulting precipitate collected, to yield the 2-methyl-4-(3,4,5-trimethoxyphenyl)-6,7-dimethoxy-9,9a-dihydro-5,6-benzoisoindoline hydrochloride hemihydrate melting at 248°–250° with decomposition.

EXAMPLE 12

Preparation of 10,000 tablets each containing 100 mg of the active ingredient:

| Formula | |
|---|---|
| 2-Methyl-4-(3,4,5-trimethoxyphenyl)-6-7-dimethoxy-9,9a-dihydro-5,6-benzoisoindoline hydrochloride hemihydrate | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene lycol in 260 ml of water. The paste formed is added to the powders which are granulated, if necessary, with an additional amount of water. The granulate is dried overnight at 35°, broken on a screen with 1.2 mm openings and compressed into tablets using concave punches with 10.3 mm diameter, uppers bisected.

We claim:

1. A pharmaceutical composition comprising an antiasthmatically effective amount of a compound of the formula

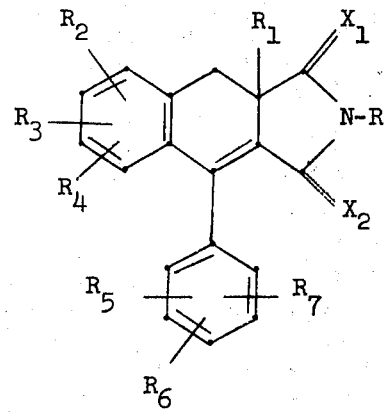

in which R is methyl or ethyl, each of $R_1$, $R_2$, $R_3$ and $R_4$ is hydrogen or methyl, each of $R_5$, $R_6$ and $R_7$ is hydrogen or methoxy, or $R_3$ and $R_4$, as well as $R_5$ and $R_6$, when taken together, are methylenedioxy, and $R_2$ and $R_7$ are hydrogen, whereby at least one of $R_1$ to $R_7$ being different from hydrogen, and both of $X_1$ and $X_2$ are two hydrogen atoms, or a therapeutically acceptable acid addition salt thereof, together with a pharmaceutical excipient.

2. A composition as claimed in claim 1, wherein the effective compound is the 2-methyl-4-(3,4,5-trimethoxyphenyl)-9,9a-dihydro-5,6-benzoisoindoline, or a therapeutically acceptable acid addition salt thereof.

* * * * *